(12) United States Patent
Woodard et al.

(10) Patent No.: US 8,167,204 B2
(45) Date of Patent: *May 1, 2012

(54) WIRELESS DAMAGE LOCATION SENSING SYSTEM

(75) Inventors: Stanley E. Woodard, Hampton, VA (US); Bryant Douglas Taylor, Smithfield, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 743 days.

This patent is subject to a terminal disclaimer.

(21) Appl. No.: 12/253,422

(22) Filed: Oct. 17, 2008

(65) Prior Publication Data

US 2009/0109005 A1 Apr. 30, 2009

Related U.S. Application Data

(60) Provisional application No. 60/981,179, filed on Oct. 19, 2007.

(51) Int. Cl.
*G06K 7/08* (2006.01)
(52) U.S. Cl. ......................... 235/449; 235/435
(58) Field of Classification Search .................. 235/384, 235/435, 439, 449, 450, 487, 492
See application file for complete search history.

(56) References Cited

U.S. PATENT DOCUMENTS

| | | | |
|---|---|---|---|
| 3,755,803 A * | 8/1973 | Cole et al. .................. | 340/572.1 |
| 4,929,896 A * | 5/1990 | Lara .............................. | 324/240 |
| 5,049,704 A | 9/1991 | Matouschek | |
| 5,285,734 A | 2/1994 | MacPherson | |
| 5,506,566 A | 4/1996 | Oldfield | |
| 5,541,577 A | 7/1996 | Cooper et al. | |
| 5,675,319 A | 10/1997 | Rivenbert et al. | |
| 5,705,981 A | 1/1998 | Goldman | |
| 5,881,310 A * | 3/1999 | Airhart et al. ..................... | 710/3 |
| 6,025,129 A * | 2/2000 | Nova et al. ....................... | 506/28 |
| 6,515,587 B2 | 2/2003 | Herbert | |
| 6,834,251 B1 * | 12/2004 | Fletcher ........................ | 702/150 |
| 6,963,281 B2 | 11/2005 | Buckley | |
| 6,995,669 B2 | 2/2006 | Morales | |
| 7,086,593 B2 * | 8/2006 | Woodard et al. .............. | 235/449 |
| 7,135,973 B2 | 11/2006 | Kittel et al. | |
| 7,159,774 B2 | 1/2007 | Woodard et al. | |

(Continued)

OTHER PUBLICATIONS

U.S. Appl. No. 11/671,089, filed Aug. 9, 2007, Woodard et al.

(Continued)

*Primary Examiner* — Daniel St.Cyr
(74) *Attorney, Agent, or Firm* — Robin W. Edwards

(57) ABSTRACT

A wireless damage location sensing system uses a geometric-patterned wireless sensor that resonates in the presence of a time-varying magnetic field to generate a harmonic response that will experience a change when the sensor experiences a change in its geometric pattern. The sensing system also includes a magnetic field response recorder for wirelessly transmitting the time-varying magnetic field and for wirelessly detecting the harmonic response. The sensing system compares the actual harmonic response to a plurality of predetermined harmonic responses. Each predetermined harmonic response is associated with a severing of the sensor at a corresponding known location thereof so that a match between the actual harmonic response and one of the predetermined harmonic responses defines the known location of the severing that is associated therewith.

24 Claims, 8 Drawing Sheets

U.S. PATENT DOCUMENTS

| | | |
|---|---|---|
| 7,194,912 B2 | 3/2007 | Oglesby et al. |
| 7,278,324 B2 | 10/2007 | Smits et al. |
| 2005/0011163 A1 | 1/2005 | Ehrensvard |
| 2006/0195705 A1 | 8/2006 | Ehrensvard et al. |
| 2006/0250239 A1 | 11/2006 | Melton |
| 2007/0183110 A1 | 8/2007 | Woodard et al. |

OTHER PUBLICATIONS

U.S. Appl. No. 11/856,807, Woodard et al.

* cited by examiner

US 8,167,204 B2

WIRELESS DAMAGE LOCATION SENSING SYSTEM

Pursuant to 35 U.S.C §119, the benefit of priority from provisional application 60/981,179, with a filing date of Oct. 19, 2007, is claimed for this non-provisional application, and the specification thereof is incorporated in its entirety herein by reference.

CROSS-REFERENCE TO RELATED PATENT APPLICATIONS

This patent application is co-pending with one related patent application entitled "WIRELESS TAMPER DETECTION SENSOR AND SENSING SYSTEM," Ser. No. 11/864,012, filed Sep. 28, 2007, by the same inventors and owned by the same assignee as this patent application.

ORIGIN OF THE INVENTION

This invention was made in part by an employee of the United States Government and may be manufactured and used by or for the Government of the United States of America for governmental purposes without the payment of any royalties thereon or therefor.

BACKGROUND OF THE INVENTION

1. Field of the Invention

This invention relates to wireless sensors and sensing systems. More specifically, the invention is a wireless damage location sensing system utilizing an open-circuit, electrically-conductive geometric-pattern sensor having no electrical connections.

2. Description of the Related Art

A variety of package tampering or damage detection systems have been developed in recent years. In general, these various systems are designed to allow a manufacturer, shipper and/or vendor/retailer to detect if a package has been tampered with (e.g., package is opened, contents are removed, and package is resealed to conceal the pilferage) in an effort to determine where there may be a problem in the finished-product shipping and warehousing chain. However, while damage detection may be sufficient for these applications, there are many applications where the mere detection of damage is not enough. That is, in many applications, the location of damage most also be known.

SUMMARY OF THE INVENTION

Accordingly, it is an object of the present invention to provide a wireless damage location sensing system.

Another object of the present invention is to provide a damage location sensing system that uses a sensor requiring no electrical connections so that the sensor can be powered and interrogated from a remote location.

Other objects and advantages of the present invention will become more obvious hereinafter in the specification and drawings.

In accordance with the present invention, a wireless damage location sensing system uses a wireless sensor defined by an electrical conductor shaped to form a geometric pattern between first and second ends thereof. The conductor in its geometric pattern defines an open-circuit that can store and transfer electrical and magnetic energy. The conductor resonates in the presence of a time-varying magnetic field to generate a harmonic response that will experience a change when the conductor experiences a change in its geometric pattern. The sensing system also includes a magnetic field response recorder for wirelessly transmitting the time-varying magnetic field and for wirelessly detecting the harmonic response. The sensing system compares the actual harmonic response to a plurality of predetermined harmonic responses. Each predetermined harmonic response or change in predetermined response is associated with a severing of the conductor at a corresponding known location along the conductor. That is, the severing changes the geometric pattern of the conductor. As a result, a match between the actual harmonic response and one of the predetermined harmonic responses defines the known location of the severing that is associated therewith.

DETAILED DESCRIPTION OF THE INVENTION

Figure 1:
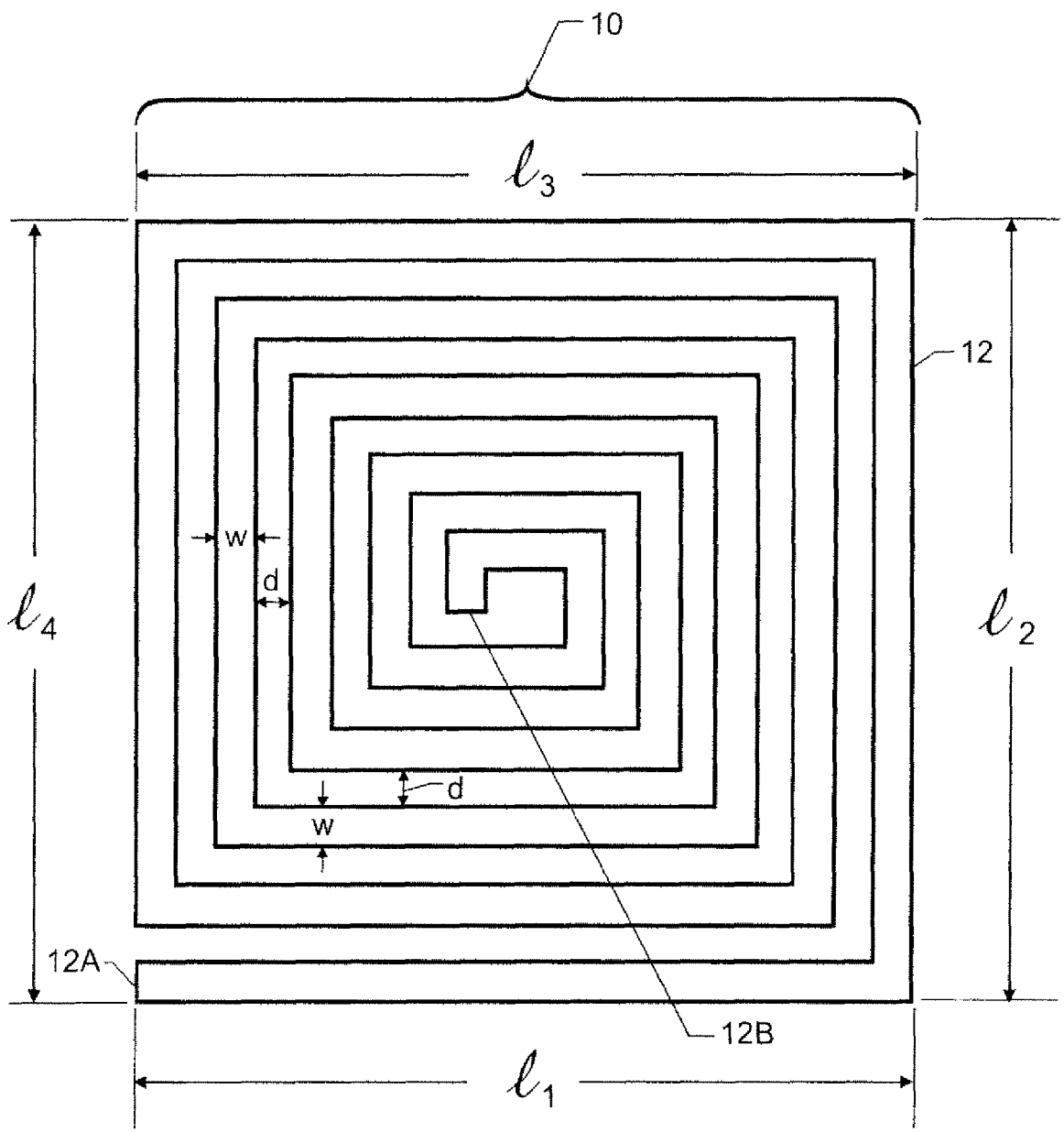
FIG. 1 is a schematic view of an embodiment of a wireless sensor used by the damage location sensing system of the present invention.

Prior to describing the wireless damage location sensing system of the present invention, several embodiments of a wireless sensor used by the present invention will be described. Referring now to the drawings and more particularly to FIG. 1, an embodiment of a wireless sensor for use with the damage location sensing system of the present invention is shown and is referenced generally by numeral 10. In this illustrated embodiment, sensor 10 comprises an open-circuit spiral trace sensor 12. However, it is to be understood that an open-circuit sensor in the present invention can be any geometric pattern made from any electrically-conductive material such that the geometric pattern can store and transfer electrical and magnetic energy when electrically excited. For the illustrated sensor 12, the trace width and spacing between adjacent trace runs have been exaggerated for purpose of illustration. Details of sensor 12 are disclosed in U.S. Patent Publication No. 2007/0181683, entitled "WIRELESS SENSING SYSTEM USING OPEN-CIRCUIT, ELECTRICALLY-CONDUCTIVE SPIRAL-TRACE SENSOR," published Aug. 9, 2007, the contents of which are hereby incorporated by reference in their entirety and are repeated herein to provide a complete description of the present invention.

Spiral trace sensor 12 is made from an electrically-conductive run or trace that can be deposited directly onto a surface (not shown) that is to be monitored for damage occurring at one or more known locations. Sensor 12 could also be deposited onto or within a substrate material (not shown) that is electrically non-conductive and can be flexible to facilitate mounting of sensor 12 to a surface. The particular choice of the substrate material(s) and substrate construction will vary depending on the application.

Sensor 12 is a spiral winding of conductive material with its ends 12A and 12B remaining open or unconnected. Accordingly, sensor 12 is said to be an open-circuit. Techniques used to deposit sensor 12 either directly onto a surface or on/in a substrate material can be any conventional metal deposition process to include thin-film fabrication techniques. In the illustrated embodiment, sensor 12 is constructed to have a uniform trace width throughout (i.e., trace width W is constant) with uniform spacing (i.e., spacing d is constant) between adjacent portions of the spiral trace. However, as will be explained further below, the present invention is not limited to a uniform width conductor spirally wound with uniform spacing.

As is well known and accepted in the art, a spiral inductor is ideally constructed/configured to minimize parasitic capacitance so as not to influence other electrical components that will be electrically coupled thereto. This is typically achieved by increasing the spacing between adjacent conductive portions or runs of the conductive spiral trace. However, in the present invention, sensor 12 is constructed/configured to have a relatively large parasitic capacitance. The capacitance of sensor 12 is operatively coupled with the sensor's inductance such that magnetic and electrical energy can be stored and exchanged by the sensor, Since other geometric patterns of a conductor could also provide such a magnetic/electrical energy storage and exchange, it is to be understood that the present invention could be realized using any such geometrically-patterned conductor and is not limited to a spiral-shaped sensor.

The amount of inductance along any portion of a conductive run of sensor 12 is directly related to the length thereof and inversely related to the width thereof. The amount of capacitance between portions of parallel conductive runs of sensor 12 is directly related to the length by which the runs overlap each other and is inversely related to the spacing between the parallel conductive runs. The amount of resistance along any portion of a conductive run of sensor 12 is directly related to the length and inversely related to the width of the portion. Total capacitance, total inductance and total resistance for spiral trace sensor 12 is determined simply by adding these values from the individual portions of sensor 12. The geometries of the various portions of the conductive runs of the sensor can be used to define the sensor's resonant frequency.

Spiral trace sensor 12 with its inductance operatively coupled to its capacitance defines a magnetic field response sensor. In the presence of a time-varying magnetic field, sensor 12 electrically oscillates at a resonant frequency that is dependent upon the capacitance, inductance and resistance of sensor 12. This oscillation occurs as the energy is harmonically transferred between the inductive portion of sensor 12 (as magnetic energy) and the capacitive portion of sensor 12 (as electrical energy). In order to be readily detectable, the capacitance, inductance and resistance of sensor 12 and the energy applied to sensor 12 from the external oscillating magnetic field should be such that the amplitude of the sensor's harmonic response exceeds that of any ambient noise by some desired level (e.g., 10 dB) where such harmonic response is being measured.

In general, for a given construction of sensor 12, the harmonic response thereof is a function of the trace pattern at the time of interrogation. That is, the entire trace pattern will yield one response whereas a lesser amount of the trace pattern will yield a different response. These various responses can be predetermined. The damage location sensing system of the present invention uses one or more of such predetermined responses in order to identify a damage location as will be explained below.

Prior to describing the use of sensor 12 in a damage location sensing system, the manner in which the sensor functions is as follows. The open-circuit, electrically conductive geometric pattern that serves as the foundation for the sensor is shown in FIG. 1. Although simple, the illustrated geometric pattern will provide the reader with a sense of how each key parameter contributes to the sensor's response. The sensor is a series of segments with each segment having a length $l_i$ and a width $w_i$. The spacing between adjacent segments $l_i$ and $l_j$ is denoted as $d_{i\_j}$ or d if the same spacing is used throughout the sensor. The sensor is powered via Faraday induction from an external oscillation magnetic field. The field magnetic flux, $\Phi_{B_{TX}}$, from the external transmitting antenna acting on the sensor is $$\Phi_{B_{TX}} = \int B_{TX} \cdot dS. \qquad (1)$$

$B_{TX}$ is a vector whose direction and magnitude are those of the magnetic field from the transmitting antenna. S is a surface vector whose direction is that of the sensor surface normal and whose magnitude is the area of the sensor surface. In accordance with Faraday's law of induction, the induced electromotive force, $\in$, on the sensor is $$\varepsilon = \frac{d\Phi_{B_{TX}}}{dt} \qquad (2)$$

The responding magnetic field, $B_{RX}$, of the geometric pattern (sensor) at any point in space is due to the combined response of each element, $dl_i$, along all the sensor segments, $l_i$. Each element, $dl_i$, is a distance $r_i$ from a point on a receiving antenna (not shown). An angle, θ, is formed by the line from the element to the point on the antenna and the direction of the current flowing through $dl_i$. The interrogated response is the result of the response of all $dl_i$ creating a magnetic flux acting upon the receiving antenna.

In accordance with the Biot-Savart Law for induction, for N sensor segments, when a sensor is electrically excited via Faraday induction, the magnetic field response $B_{RX}$ produced by the sensor at any point in space is $$B_{RX} = \left[\frac{\mu}{4\pi}\right]\left[\frac{\frac{d\Phi_{B_{TX}}}{dt}\big|_{t_\theta}}{\sqrt{S^2+R^2}}\right]\sum_{i=1}^{N}\int_{l_i}\frac{dl_i\sin\theta_i}{r_i^2}. \quad (3a)$$

The damped natural frequency, $\omega_d$, is dependent upon resistance of the sensor and is $$\omega_d = \sqrt{\omega_n^2 - \frac{1}{2}\left(\frac{R}{L}\right)^2} \quad (3b)$$

with $$\omega_n = \frac{1}{2\pi\sqrt{LC}}. \quad (3c)$$

$L_i$ and $R_i$ along the ith segment of the sensor are the respective contributions to the total inductance and resistance:

$$L = \sum_{i=1}^{N} L_i \quad (4)$$

$$R = \sum_{i=1}^{N} R_i \quad (5)$$

The capacitance $C_{[2(i-1)+1][2j+1]}$ between the parallel vertical segments is the result of the electric field between the segments $[2(i-1)+1]$ and $[2j+1]$. Similarly, the capacitance between parallel horizontal segments is $C_{[2(i-1)+2][2j+2]}$. The total capacitance, C, is $$C = \sum_{i=1}^{N_v-1}\sum_{j=1}^{N_v-1} C_{[2(i-1)+1][2j+1]} + \sum_{i=1}^{N_h-1}\sum_{j=1}^{N_h-1} C_{[2(i-1)+2][2j+2]} \quad (6)$$

where $N_v$ and $N_h$ are the number of vertical and horizontal segments, respectively, and $$S = \left(\omega L - \frac{1}{\omega C}\right). \quad (7)$$

The capacitance increases as the space between neighboring segments, $d_{i\_j}$, decreases.

The methods of powering and interrogating magnetic field response sensors (discussed further below) create the variational magnetic flux, $$\frac{d\Phi_{B_{TX}}}{dt},$$

that induces the electromotive force, $\in$, in each sensor and receives the response from each sensor. The response damped natural frequency, $\omega_d$, and the response amplitude of each sensor is what is interrogated. When the sensor is excited with magnetic field harmonics whose frequency is that of the damped natural frequency, the sensor magnetic field response will be at its maximum amplitude.

The sensor's resistance, R, is dependent upon temperature, T, and can be referenced to a baseline minimum temperature, $T_{min}$, by the following relationship $$R = [R_{min}[1+\alpha(T-T_{min})]] \quad (8)$$

where $R_{min}$ is the sensor minimum resistance at $T_{min}$, and $\alpha$ is material dependent. For copper this is $$\alpha = \frac{1}{(234.5+T_{min})}. \quad (9)$$

Any temperature can be used for $T_{min}$. For example, if the minimum resistance, $R_{min}$, occurs at $T_{min}=0°$ C., then $\alpha=0.00427$. The sensor response, $B_{RX}=B_{RX}(T)$, is dependent upon temperature for fixed capacitance and inductance by the following relation $$B_{RX}(T) = \left[\frac{\mu}{4\pi}\right]\left[\frac{\frac{d\Phi_{B_{TX}}}{dt}\big|_{t_0}}{\sqrt{S^2+[R_{min}[1+\alpha(T-T_{min})]]^2}}\right]\sum_{i=1}^{N}\int_{l_i}\frac{dl_i\sin\theta_i}{r_i^2}. \quad (10a)$$

Similarly, the damped natural frequency, $\omega_d$, is $$\omega_d = \sqrt{\omega_n^2 - \frac{1}{2}\left(\frac{[R_{min}[1+\alpha(T-T_{min})]]}{L}\right)^2}. \quad (10b)$$

$B_{RX}(T)$ and $\omega_d$ are dependent on temperature, inductance, capacitance, and resistance at a reference temperature in degrees Celsius. As the temperature increases from $T_{min}$, the damped natural frequency and response amplitude monotonically decrease, while the bandwidth increases.

The temperature can also be directly correlated to the response bandwidth using the following method. Briefly, once the resonant frequency and its respective amplitude for a particular sensor have been identified, the response amplitude produced using the harmonic at a prescribed number prior to that producing the maximum response is then acquired. The resistance is inversely proportional to the difference of the amplitudes, The bandwidth of the response is proportional to the circuit resistance However, to measure bandwidth, one would need to identify the response peak and then measure the response curve on either side of the peak to ascertain the 3 dB reductions in amplitude. To identify the 3 dB reduction would require measuring all amplitudes for each discrete harmonic until the reduction amplitudes are identified. A simplified method can be used to measure resistance by examining how much the amplitude is reduced from the maximum at a fixed frequency separation, $\Delta\omega$, from the resonant frequency, $\omega_d$.

The sensor has a fissiparous nature that can be exploited for damage and tamper detection. If the sensor is broken or torn such that segments $l_k$ through $l_m$ are severed from the pattern, the single sensor of Equations (10a) and (10b) will result in two concentric and inductively coupled sensors whose responses when not inductively coupled are $B_{RX_1}(T)$ and $B_{RX_2}(T)$ with $$B_{RX_1}(T) = \left[\frac{\mu}{4\pi}\right]\left[\frac{\frac{d\Phi_{B_{TX}}}{dt}\big|_{t_0}}{\sqrt{S_1^2 + [R_{1min}[1 + \alpha(T - T_{min})]]^2}}\right]\sum_{i=1}^{N}\int_{l_i}\frac{dl_i \sin\theta_i}{r^2} \quad (11a)$$

$$\omega_{d_1} = \sqrt{\omega_n^2 - \frac{1}{2}\left(\frac{[R_{1min}[1 + \alpha(T - T_{min})]]}{L_1}\right)^2} \quad (11b)$$

with $$S_1 = \left(\omega L_1 - \frac{1}{\omega C_1}\right); L_1 = \sum_{i=1}^{k} L_{1i}; R_1 = \sum_{i=1}^{k} R_{1i}$$

and $$C_1 = \sum_{i=1}^{N_{1v}-1}\sum_{j=i}^{N_{1v}-1} C_{[2(i-1)+1][2j+1]} + \sum_{i=1}^{N_{1h}-1}\sum_{j=i}^{N_{1h}-1} C_{[2(i-1)+2][2j+2]}$$

$$B_{RX_2}(T) = \left[\frac{\mu}{4\pi}\right]\left[\frac{\frac{d\Phi_{B_{TX}}}{dt}\big|_{t_0}}{\sqrt{S_2^2 + [R_{2min}[1 + \alpha(T - T_{min})]]^2}}\right]\sum_{i=m}^{N}\int_{l_i}\frac{dl_i \sin\theta}{r^2} \quad (12a)$$

$$\omega_{d_2} = \sqrt{\omega_{n2}^2 - \frac{1}{2}\left(\frac{[R_{1min}[1 + \alpha(T - T_{min})]]}{L_2}\right)^2} \quad (12b)$$

$$S_2 = \left(\omega L_2 - \frac{1}{\omega C_2}\right); L_2 = \sum_{i=m}^{n} L_{2i}; R_2 = \sum_{i=m}^{n} R_{2i}$$

and $$C_2 = \sum_{i=1}^{N_{2v}-1}\sum_{j=i}^{N_{2v}-1} C_{[2(i-1)+1][2j+1]} + \sum_{i=1}^{N_{2h}-1}\sum_{j=i}^{N_{2h}-1} C_{[2(i-1)+2][2j+2]}.$$

The subscripts 1i and 2i index the ith segments of the two inductively coupled sensors, respectively. The resulting response frequency for the two new patterns will each have a higher frequency than the original sensor because each has less inductance and capacitance. Should there be a subsequent severing on any segments along the remaining sensors, that single sensor will result in two concentric sensors in a similar manner.

Figure 2:
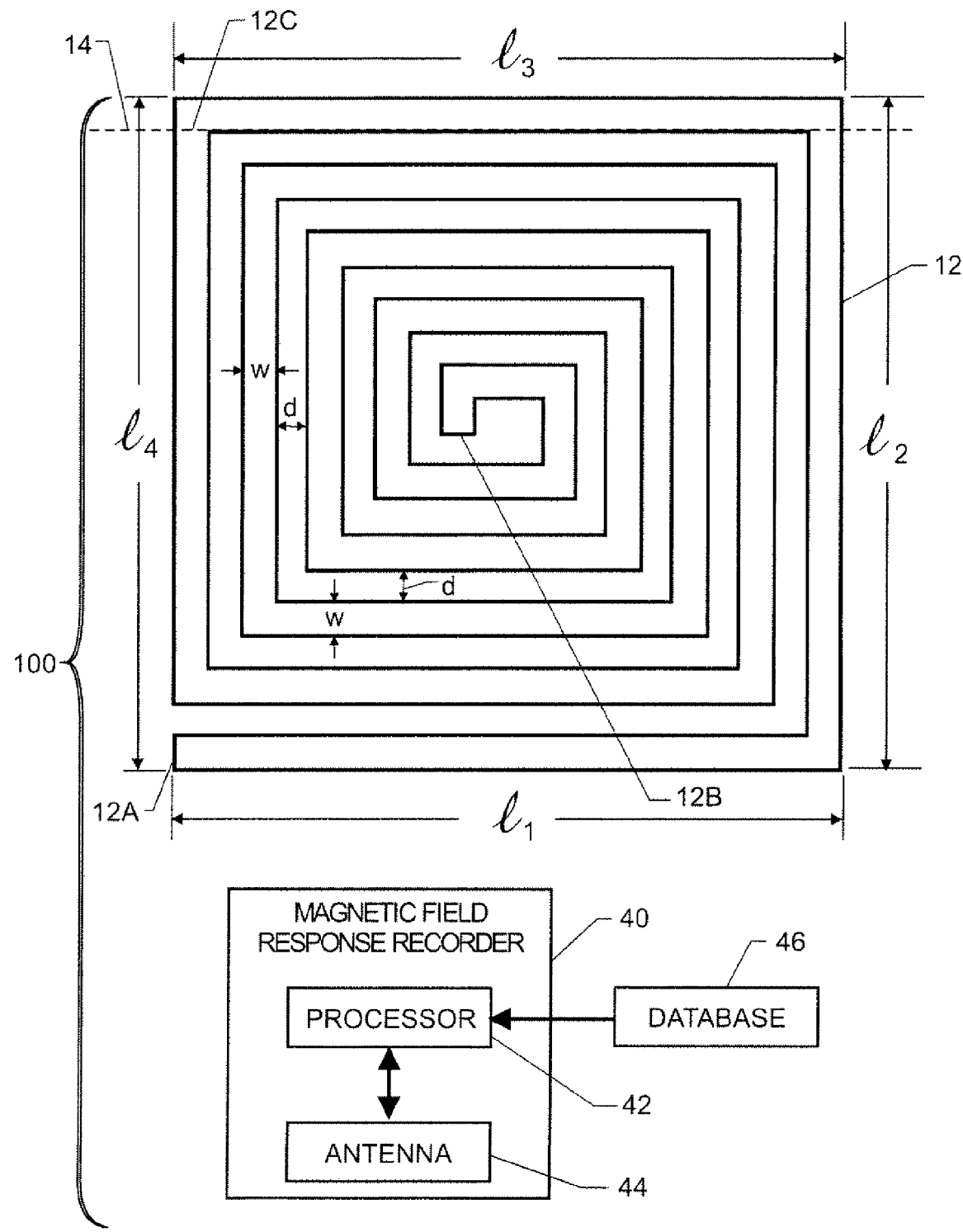
FIG. 2 is a schematic view of a damage location sensing system in accordance with an embodiment of the present invention.

Referring now to FIG. 2, a damage location sensing system in accordance with an embodiment of the present invention is shown and is referenced generally by numeral 100. By way of example, the wireless sensor is sensor 12 described above. However, it is to be understood that other sensors could be used with several examples of same being described later herein.

Figure 3:
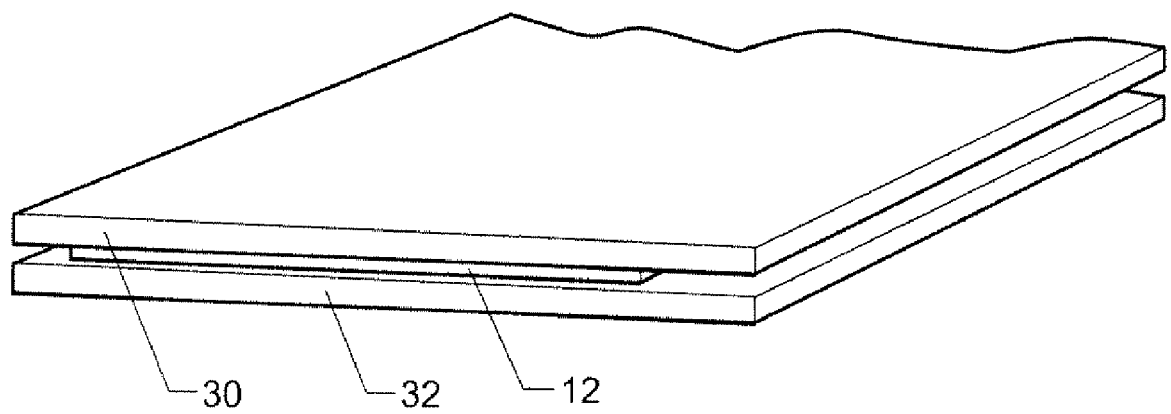
FIG. 3 is a perspective view of a wireless sensor mounted between two layers of a substrate in accordance with another embodiment of the present invention.

As mentioned above, the sensor in the present invention can be deposited/formed directly on a surface that is to be monitored. However, the sensor could also be disposed or captured between two layers 30 and 32 of a substrate material as illustrated in FIG. 3 where a perspective view of the layered structure is shown. In this embodiment, sensor 12 is hidden from view and is protected by layers 30 and 32. One or both of layers 30 and 32 can be a non-conductive tearable (e.g., paper) or tear-resistant (e.g., plastic, wood, ceramic, reinforced tape, etc.) without departing from the scope of the present invention.

The application of a time-varying magnetic field to sensor 12 as well as the reading of the induced harmonic response at a resonant frequency is accomplished by a magnetic field response recorder 40. The operating principles and construction details of recorder 40 are provided in U.S. Pat. Nos. 7,086,593 and 7,159,774, S. E. Woodard, B. D. Taylor, "Measurement of Multiple Unrelated Physical Quantities Using a Single Magnetic Field Response Sensor," Meas, Sci. Technol. 18 (2007) 1603-1613, and S. E. Woodard, B. D. Taylor, Q. A. Shams, R. L. Fox, "Magnetic Field Response Measurement Acquisition System," NASA Technical Memorandum 2005-213518, the contents of each being hereby incorporated by reference in their entirety.

Briefly, magnetic field response recorder 40 includes a processor 42 and a broadband radio frequency (RF) antenna 44 capable of transmitting and receiving RF energy. Processor 42 includes algorithms embodied in software for controlling antenna 44 and for analyzing the RF signals received from the magnetic field response sensor defined by either the intact or severed form of sensor 12 in accordance with the present invention. On the transmission side, processor 42 modulates an input signal that is then supplied to antenna 44 so that antenna 44 produces either a broadband time-varying magnetic field or a single harmonic field. On the reception side, antenna 44 receives harmonic magnetic responses produced by sensor 12. Antenna 44 can be realized by two separate antennas or a single antenna that is switched between transmission and reception. The actual construction details of recorder 40 will vary with the particular operational scenario. For example, recorder 40 can be hand-held, mounted on a robot, or mounted to a piece of handling equipment (e.g., conveyor, lift, shelf, etc.) without departing from the scope of the present invention.

In accordance with the present invention, a database 46 of known harmonic responses is also provided and must be accessible by or incorporated with processor 42. Database 46 stores a predetermined harmonic response associated with the entirety or "in tact" form of sensor 12 as well as a predetermined harmonic response associated with at least one severed form of sensor 12. For example, system 100 can be used in a grinding or milling operation with sensor 12 positioned on a specimen (not shown) that is to be milled down to a level indicated by dashed line 14. When this occurs, the outside three legs/traces of sensor 12 of lengths $l_1$-$l_3$ are severed from the original sensor so that the remaining spiral extends from end 12B to new end 12C. Therefore, in this example, database 46 would store the predetermined harmonic responses associated with the entirety of sensor 12 (i.e., extending from end 12A to end 12B) and the severed form of sensor 12 (i.e., extending from end 12C to end 12B). During the milling operation, recorder 40 could continuously or periodically interrogate sensor 12 and compare the actual harmonic response with those stored in database 46. Once a match occurred between the actual harmonic response and the predetermined response associated with the location of line 14, the proper milled level is indicated. The generated match could be used to generate a signal for an operator or could be used as feedback control in an automated milling system. A similar approach could be used for a wear detection system (e.g., brake wear, etc.).

Figure 4:
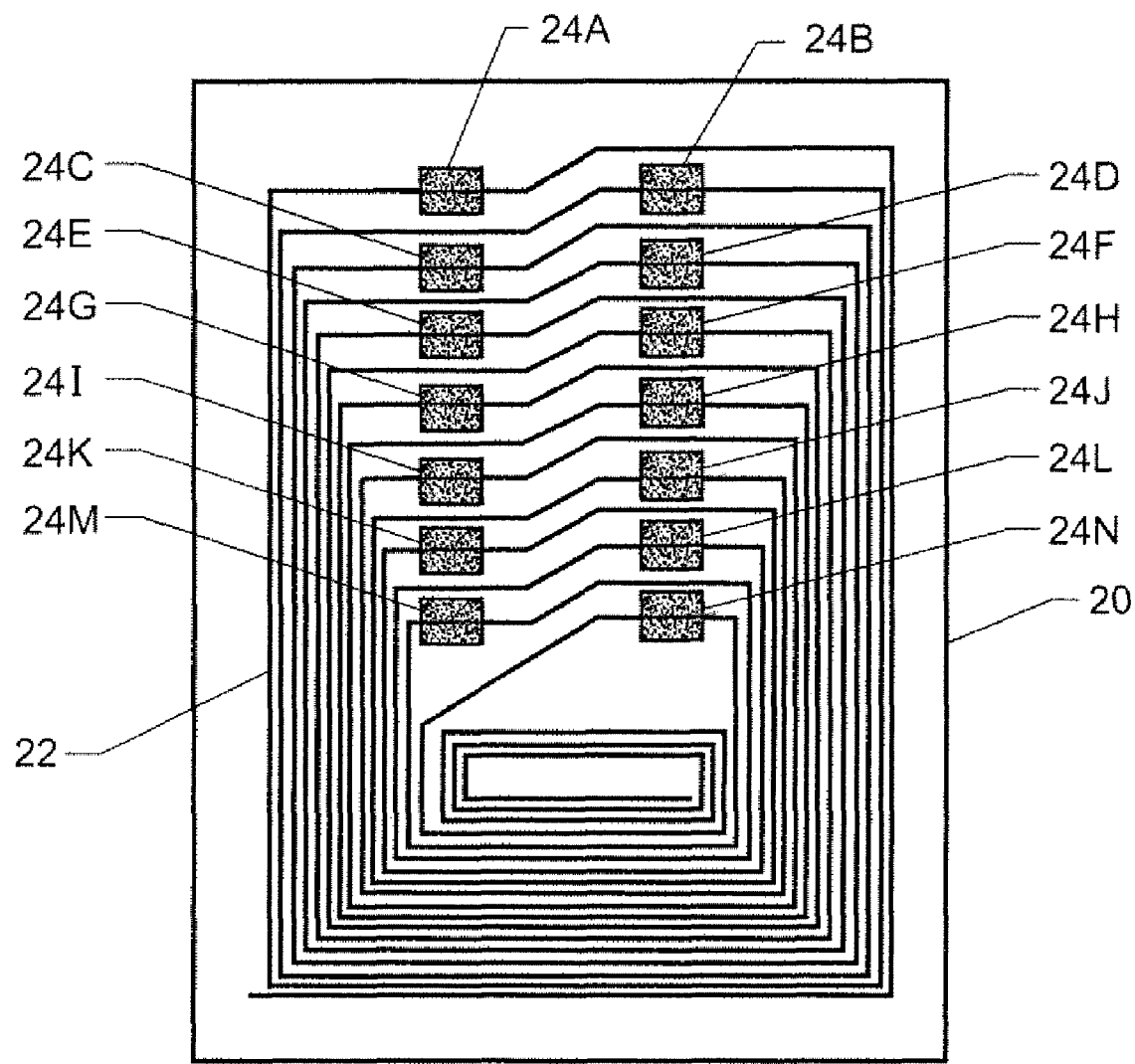
FIG. 4 is a schematic view of a multiple damage point location sensing system in accordance with another embodiment of the present invention.
Figure 4:
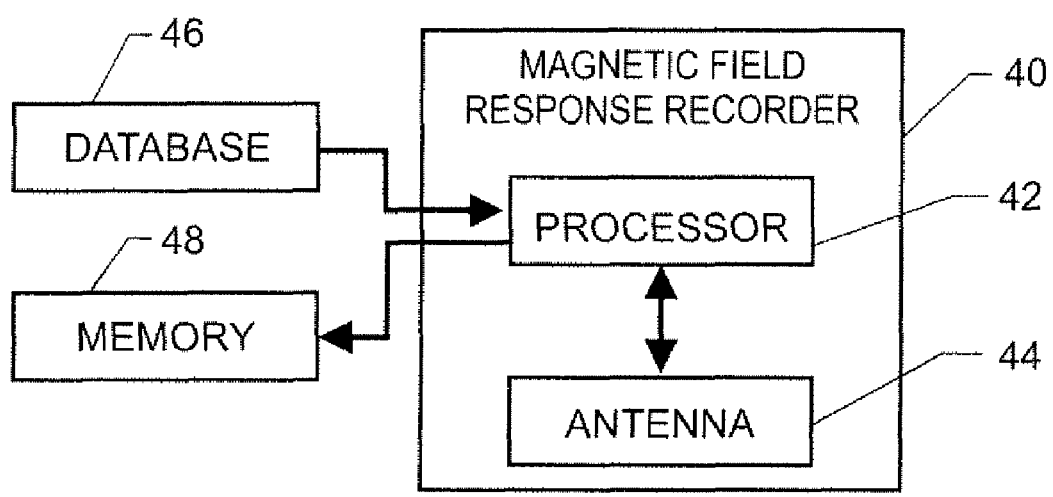

The present invention could also be used to identify a plurality of known sequential damage locations. By way of example, one such application is illustrated in FIG. 4 where a spiral sensor 22 is mounted on a backing sheet 20 (i.e., a substrate). The proper damage sequence is indicated by rectangular boxes 24A-24N where box 24A indicates the location of the first damage location, box 24B indicates the position of the second damage location, etc. Each box 24A-24N would typically define lines of perforations formed in backing sheet 20. The box could also be used to define a specific damage location. As is well known in the art, one or more items (not shown) are housed in a chamber (not shown) covered by the portion of backing sheet 20 defined by one of boxes 24A-24N. An item inside the box is dispensed by pushing it from its chamber through backing sheet 20 at one of boxes 24A-24N as would be well understood in the art. Sensor 22 and boxes 24A-24N are arranged so that the conductive-trace sensor 22 is spiraled through boxes 24A-24N in the proper dispensing sequence. In this way, each of boxes 24A-24N defines a severing location of the sensor's conductive trace. Each such severing location will have a harmonic response associated therewith that can be predetermined and stored in database 46.

In an exemplary operation of the system shown in FIG. 4, recorder 40 could be configured to periodically (e.g., at 9 AM and 9 PM each day) interrogate sensor 22. The actual harmonic response recorded at a particular interrogation would be compared with a particular predetermined harmonic response stored in database 46. For example, at the time all items inside all boxes were given to a user, recorder 40 could be operated to compare the actual harmonic response with the predetermined response associated with the entirety of sensor 22. This initial interrogation could be used to initiate subsequent and periodic interrogations of sensor 22. That is, each subsequent interrogation would include a comparison between the current actual harmonic response and harmonic response associated with the next of boxes 24A-24N (i.e., damage location). Each interrogation/comparison would yield one of three results. If the dispensing of individual items was timely and in the proper sequence, a match will occur between the actual harmonic response and the predetermined harmonic response associated with the particular interrogation in the sequence. However, no such match will occur if the dispensing of the box contents did not take place or was out of sequence. In either of these non-match cases, an alarm could be triggered or time stored in memory. Additionally or alternatively, the actual harmonic responses could be stored in a memory 48 coupled to or incorporated with processor 42. The actual harmonic responses could also have a date/time (i.e., a time stamp) recorded therewith.

The above-described applications are not to be considered limitations of the present invention. For example, a wireless sensor of the present invention could be applied to a ticket that was to be punched by a human or a machine. Such tickets are used on toll roads, onboard passenger trains, etc.

Figure 5:
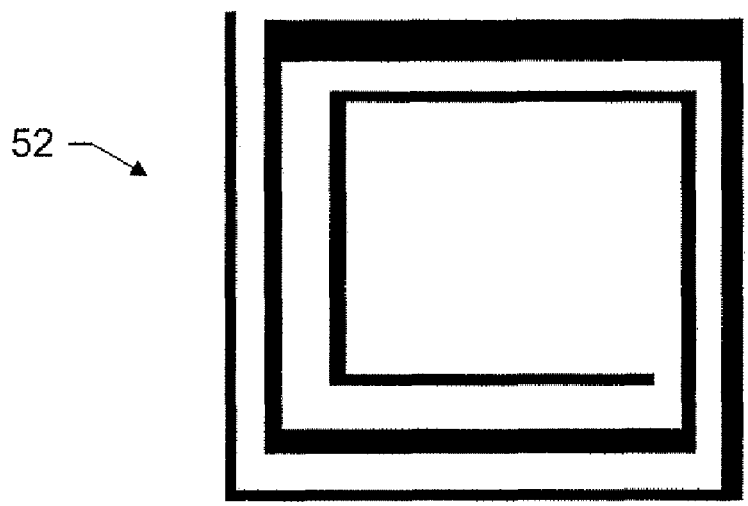
FIG. 5 is a schematic view of a spiral trace sensor whose traces are non-uniform in width.
Figure 6:
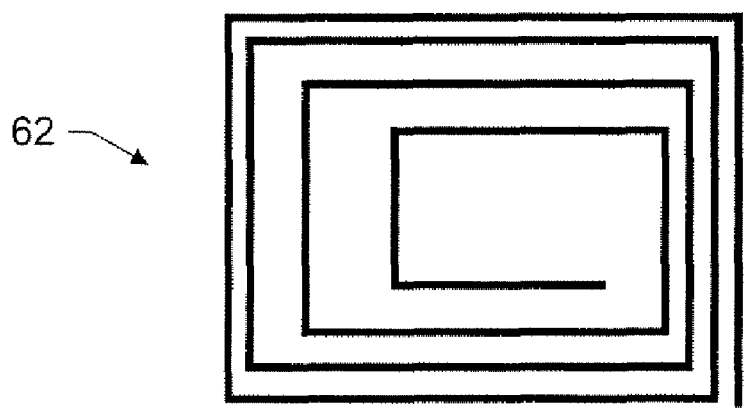
FIG. 6 is a schematic view of a spiral trace sensor having non-uniform spacing between the traces thereof.
Figure 7:
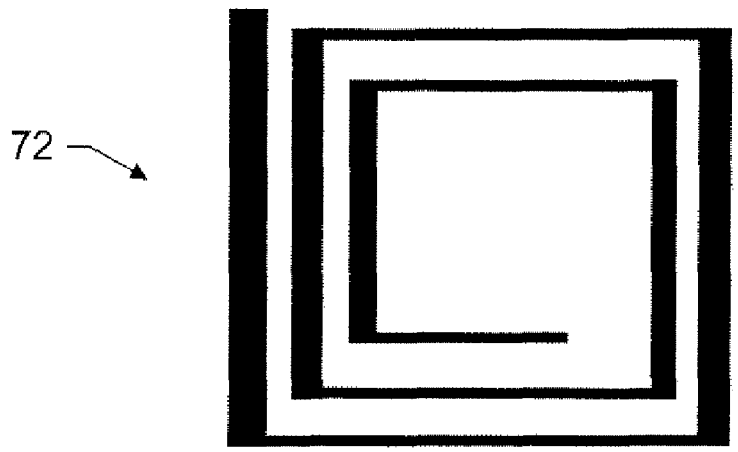
FIG. 7 is a schematic view of a spiral trace sensor having non-uniform trace width and non-uniform trace spacing.

As mentioned above, both the width of the sensor's conductive trace and the spacing between adjacent portions of the conductive trace can be uniform as shown in FIG. 1. However, the present invention is not so limited as will be shown by the following three examples. Simple sensor traces are shown for these three examples to simplify the drawings thereof. FIG. 5 illustrates a sensor 52 in which the width of the conductive trace is non-uniform while the spacing between adjacent portions of the conductive trace is uniform. FIG. 6 illustrates a sensor 62 in which the width of the conductive trace is uniform, but the spacing between adjacent portions of the conductive trace is non-uniform. Finally, FIG. 7 illustrates a sensor 72 having both a non-uniform width conductive trace and non-uniform spacing between adjacent portions of the conductive trace.

As described above, the length/width of the conductive trace and the spacing between adjacent portions of the conductive trace determine the capacitance and inductance (and, therefore, the resonant frequency) of a spiral trace sensor in the present invention. In addition, the sensor's resonant frequency can be modified by providing a dielectric material (i) that resides between adjacent portions of the sensor's conductive trace, or (ii) that encases the sensor's conductive trace. In a similar manner, other electrically conductive geometric patterns that can store both electric and magnetic energy can be tailored geometrically to prescribe a desired frequency.

Previously-cited U.S. Patent Publication No. 2007/0181683 discusses methods by which an arrangement of open-circuit sensors can be in close enough proximity to one another such that they are inductively coupled to each other. This type of arrangement allows the measurement of each sensor to be interrogated by a magnetic field response recorder without the recorder's magnetic field directly interrogating each sensor. That is, just one sensor can be powered directly by the recorder, and the recorder can directly receive the response (for the whole arrangement) from this sensor. The remaining sensors in the arrangement are communicated with via inductive coupling as their response is superimposed upon that of the sensor being powered and interrogated directly. Hence, the sensor being directly powered/interrogated has a response containing the resonant responses of all sensors in the arrangement that are inductively coupled thereto. Two simple damage location sensing arrangements using multiple sensors are shown in FIGS. 8A and 8B.

Figure 8A:
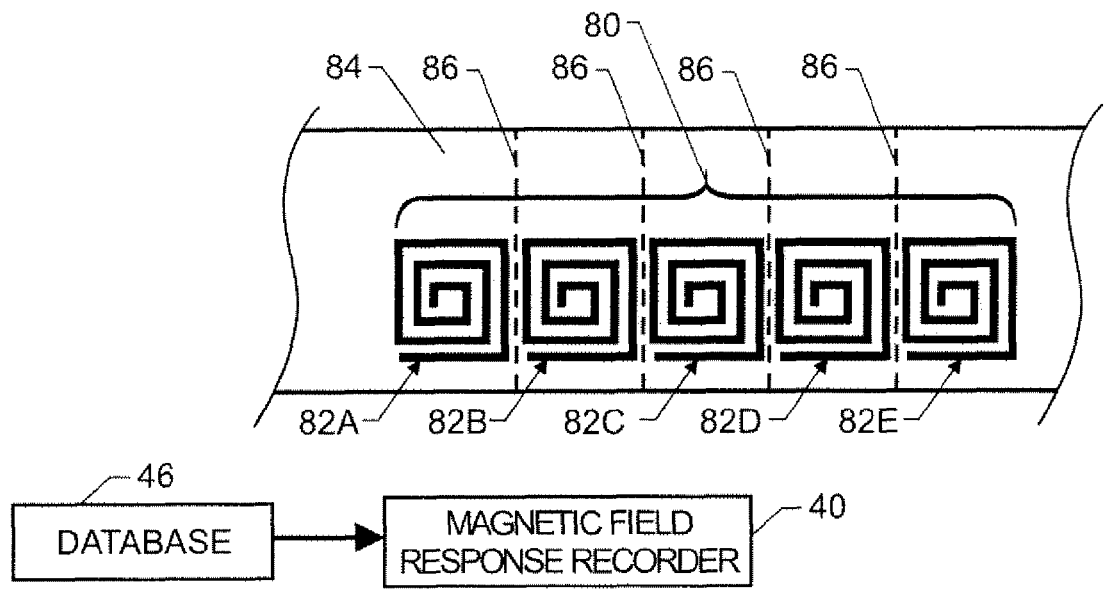
FIG. 8A is a schematic view of a linear arrangement of open-circuit spiral trace sensors that can be mutually inductively coupled and interrogated by a magnetic field response recorder.

FIG. 8A illustrates an arrangement 80 of spiral trace sensors 82A-82E all aligned in a row where magnetic field response recorder 40 is positioned to power and receive responses from sensor 82A. Sensors 82A-82E are deposited on a substrate 84 with a number of predetermined damage locations referenced by dashed lines 86. The actual harmonic response recorded by recorder 40 will depend on which of sensors 82A-82E are inductively coupled. When there is no damage and all sensors 82A-82E are inductively coupled, their response will be superimposed upon the response of an interrogated one of the sensors (e.g., sensor 82A) via inductive coupling. Each sensor is designed so that its frequency does not overlap that of any other sensor. If any one or more sensors are separated from the arrangement along one of known damage locations 86, the change will manifest itself in the response of sensor 82A.

Figure 8B:
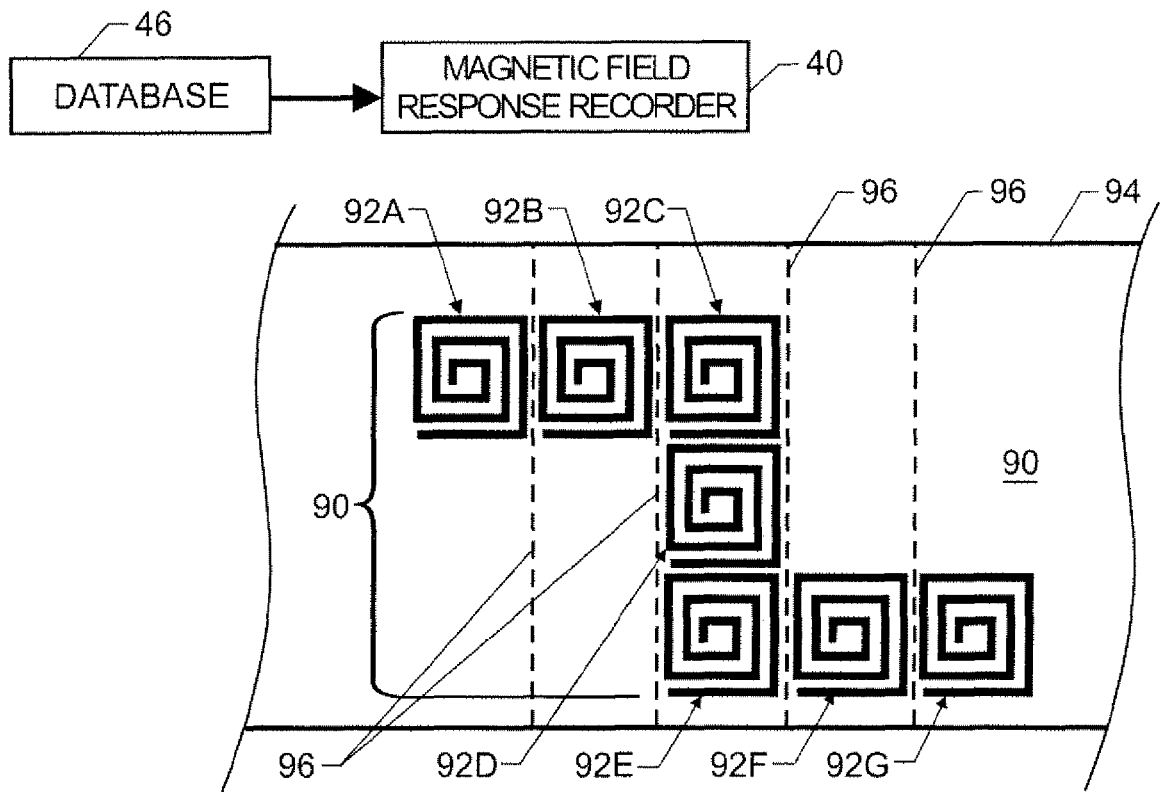
FIG. 8B is a schematic view of a non-linear arrangement of open-circuit spiral trace sensors that can be mutually inductively coupled and interrogated by a magnetic field response recorder.

FIG. 8B illustrates an arrangement 90 of spiral trace sensors 92A-92G not aligned in a row where magnetic field response recorder 40 is positioned to power and receive responses from sensor 92A. Sensors 92A-92G are deposited on a substrate 94. A representative example pattern of known damage locations in the sensor arrangement are referenced by dashed lines 96. When there is no damage, all the sensors are inductively coupled and their response will be superimposed upon the response of sensor 92A via inductive coupling. That is, the previously described approach of powering/interrogating an arrangement of sensors via inductive coupling does not require that the sensors be aligned in any particular arrangement. The only requirement for interrogating the sensors via inductive coupling is that the relative positions of the sensors remain fixed.

Figure 9A:
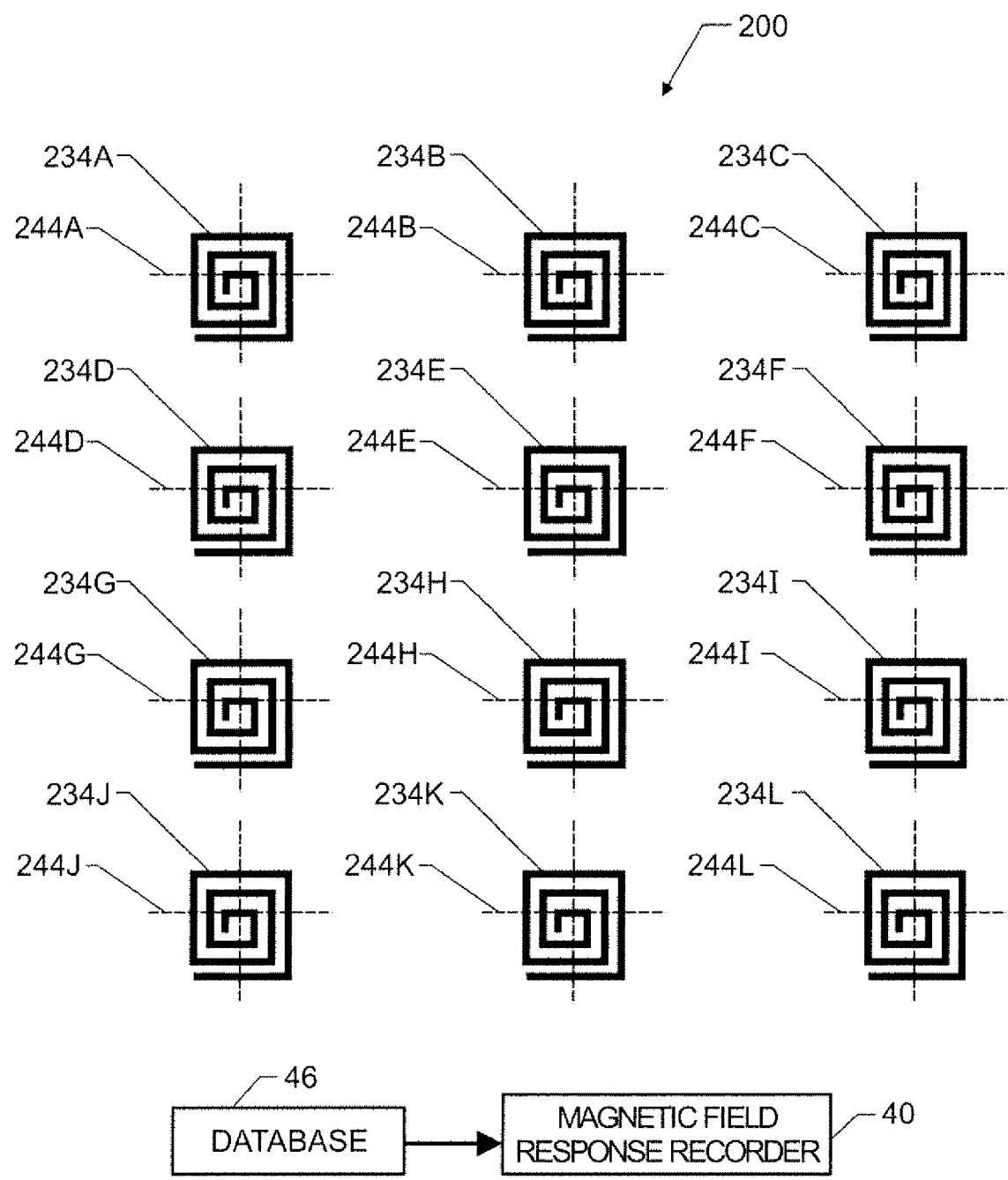
FIG. 9A is a schematic view of an arrangement of open-circuit spiral trace sensors that are non-mutually inductively coupled with a perforation box and interrogated by a magnetic field response recorder.
Figure 9B:
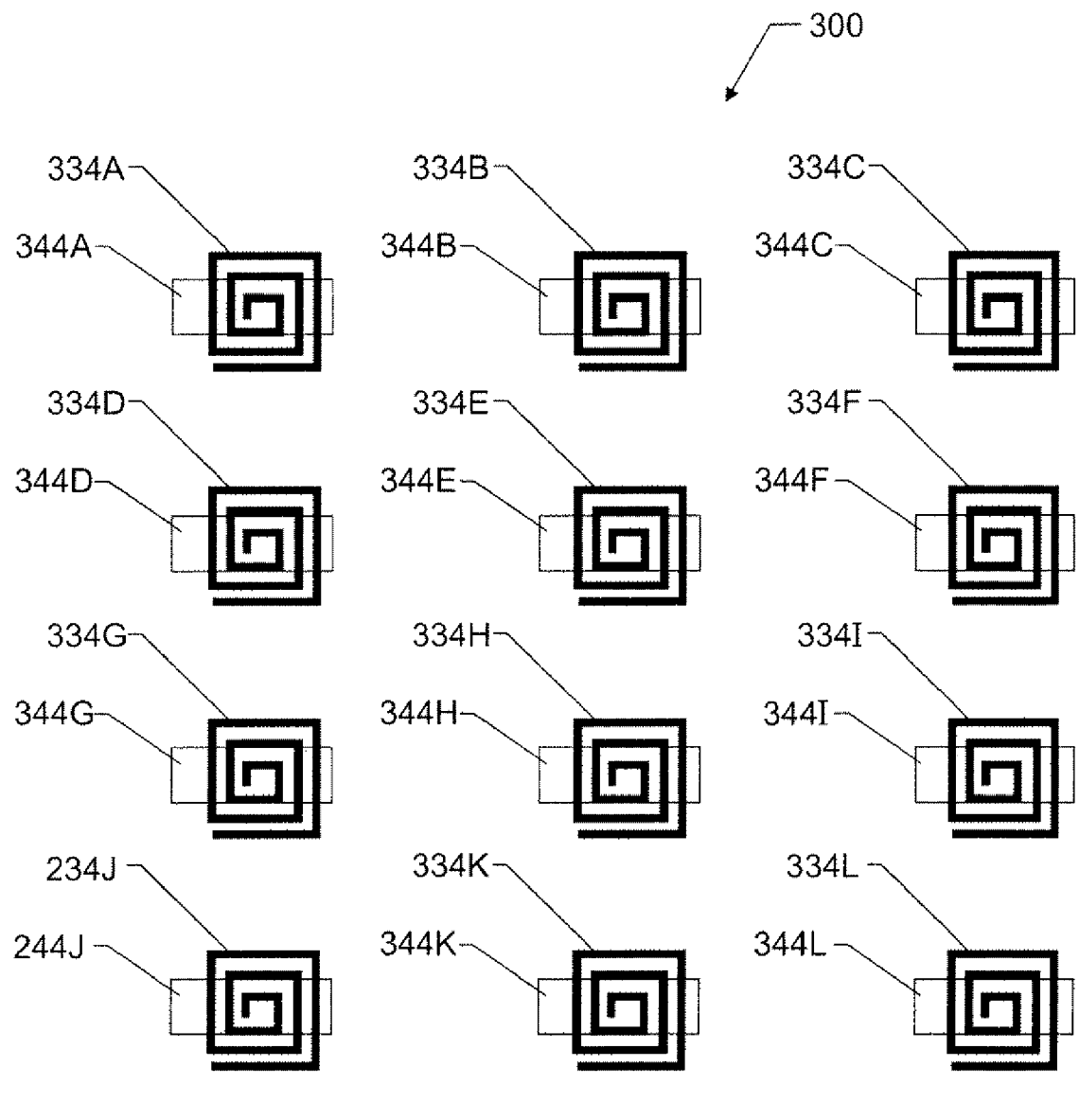
FIG. 9B is a schematic view of an arrangement of open-circuit spiral trace sensors that can be non-mutually inductively coupled with cross-hair perforation and interrogated by a magnetic field response recorder.

Two simple non-inductively coupled damage location sensing arrangements using multiple sensors are shown in FIGS. 9A and 9B. FIG. 9A illustrates an arrangement 200 of spiral trace sensors 234A-234L, all aligned in an array where magnetic field response recorder 40 is positioned to power and receive responses from each sensor. Sensors 234A-234L are deposited at predetermined damage locations referenced by dashed line cross-hairs 244A-244L. Each sensor is designed with a unique frequency range so that its frequency does not overlap that of any other sensor. Damage to each location results in a frequency shift that does not overlap with the other sensor responses at non-damaged locations. This embodiment allows determination of damage without the damage being sequential.

FIG. 9B illustrates an arrangement 300 of spiral trace sensors 334A-334L, all aligned in an array where magnetic field response recorder 40 is positioned to power and receive responses from each sensor. Sensors 334A-334L are deposited at predetermined damage locations referenced by boxes 344A-344L. Each sensor is designed with a unique frequency range so that its frequency does not overlap that of any other sensor. Damage to each location results in a frequency shift that does not overlap with the other sensor responses at non-damaged locations. This embodiment allows determination of damage without the damage being sequential.

An arrangement of non-inductively coupled sensors 22 could also be used for magnetic field response encoding system similar to a bar code, Each sensor is designed with a unique frequency range so that its frequency does not overlap that of any other sensor. Only ten potential damage locations are placed on each sensor allowing the sensor to serve as a base 10 digit. Each sensor is damaged once at one of its ten damage locations, resulting in the magnetic field response equivalent of a number. The combination of sensor responses is the equivalent of a multi-digit number with each digit derived from each sensor. A magnetic field response encoding system allows the identification numbers of items such as, but not limited to, products, components, personal badges, passports and credit cards to be interrogated wirelessly, but does not serve as a memory device that can be written to wirelessly.

The advantages of the present invention are numerous. One or more geometric-patterned open-circuit sensors can be used to indicate a particular damage location. The sensors are wirelessly powered and read by a magnetic field response recorder. The conducting portion of the sensor can be made from a lightweight conductive trace that can be readily incorporated on or into a substrate. Each damage event time can be stored and correlated with other information related to the damage event.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A wireless damage location sensing system, comprising:
   an electrical conductor having first and second ends, and shaped to form a geometric pattern between said first and second ends;
   said conductor in said geometric pattern defining an open-circuit that can store and transfer electrical and magnetic energy;
   said conductor resonating in the presence of a time-varying magnetic field to generate a harmonic response, wherein said harmonic response changes when said conductor experiences a change in said geometric pattern;
   a magnetic field response recorder (MFRR) for wirelessly transmitting said time-varying magnetic field and for wirelessly detecting said harmonic response; and
   means coupled to said MFRR for comparing said harmonic response so-generated to a plurality of predetermined harmonic responses with each of said predetermined harmonic responses being associated with a severing of said conductor at a corresponding known location along said conductor such that said severing changes said geometric pattern of said conductor, wherein a match between said harmonic response and one of said predetermined harmonic responses defines said known location of said severing associated therewith.

2. A wireless damage location sensing system as in claim 1, further comprising means for operating said MFRR on a periodic basis to generate said harmonic response with periodic frequency wherein a plurality of harmonic responses are generated.

3. A wireless damage location sensing system as in claim 2, further comprising means for storing each of said harmonic responses so-generated.

4. A wireless damage location sensing system as in claim 3, further comprising means for time-stamping each of said harmonic responses so-stored.

5. A wireless damage location sensing system as in claim 1, further comprising a substrate to which said conductor is coupled.

6. A wireless damage location sensing system as in claim 5, further comprising arrangements of perforations passing through said substrate and said conductor with each of said arrangements defining one said known location for one said severing.

7. A wireless damage location sensing system as in claim 6, wherein each of said arrangements of perforations comprises a dosed geometric shape encompassing a continuous portion of said conductor.

8. A wireless damage location sensing system as in claim 1, wherein said conductor comprises a thin-film trace defining said geometric pattern, and wherein the width of said trace is selected from the group consisting of uniform and non-uniform and the spacing between adjacent portions of said trace is selected from the group consisting of uniform and non-uniform.

9. A wireless damage location sensing system as in claim 1, wherein said geometric pattern is a spiral.

10. A wireless damage location sensing system, comprising:
    a substrate;
    an electrical conductor coupled to said substrate, said conductor having first and second ends, and shaped to form a geometric pattern between said first and second ends;
    said conductor in said geometric pattern defining an open-circuit that can store and transfer electrical and magnetic energy;
    said conductor resonating in the presence of a time-varying magnetic field to generate a harmonic response, wherein said harmonic response changes when said conductor experiences a change in said geometric pattern;
    a magnetic field response recorder (MFRR) for wirelessly transmitting said time-varying magnetic field on a periodic basis and for wirelessly detecting each said harmonic response generated by said conductor, wherein a plurality of harmonic responses are generated; and
    means coupled to said MFRR for comparing each said harmonic response so-generated to a plurality of predetermined harmonic responses with each of said predetermined harmonic responses being associated with a severing of said conductor at a corresponding known location along said conductor such that said severing changes said geometric pattern of said conductor, wherein a match between said harmonic response and one of said predetermined harmonic responses defines said known location of said severing associated therewith.

11. A wireless damage location sensing system as in claim 10, further comprising means for storing each of said harmonic responses so-generated.

12. A wireless damage location sensing system as in claim 11, further comprising means for time-stamping each of said harmonic responses so-stored.

13. A wireless damage location sensing system as in claim 10, further comprising arrangements of perforations passing through said substrate and said conductor with each of said arrangements defining one said known location for one said severing.

14. A wireless damage location sensing system as in claim 13, wherein each of said arrangements of perforations comprises a closed geometric shape encompassing a continuous portion of said conductor.

15. A wireless damage location sensing system as in claim 10, wherein said conductor comprises a thin-film trace defining said geometric pattern, and wherein the width of said trace is selected from the group consisting of uniform and non-uniform and the spacing between adjacent portions of said trace is selected from the group consisting of uniform and non-uniform.

16. A wireless damage location sensing system as in claim 10, wherein said geometric pattern is a spiral.

17. A wireless damage location sensing system, comprising:
an electrical conductor having first and second ends, and shaped to form a geometric pattern between said first and second ends;
said conductor in said geometric pattern defining an open-circuit that can store and transfer electrical and magnetic energy;
said conductor resonating in the presence of a time-varying magnetic field to generate a harmonic response, wherein said harmonic response changes when said conductor experiences a change in said geometric pattern;
a magnetic field response recorder (MFRR) for wirelessly transmitting said time-varying magnetic field and for wirelessly detecting said harmonic response;
means coupled to said MFRR for comparing said harmonic response so-generated to a plurality of predetermined harmonic responses with each of said predetetinined harmonic responses being associated with a severing of said conductor at a corresponding known location along said conductor such that said severing changes said geometric pattern of said conductor, wherein a match between said harmonic response and one of said predetermined harmonic responses defines said known location of said severing associated therewith; and
arrangements of perforations overlaid on said geometric pattern with each of said arrangements defining one said known location for one said severing.

18. A wireless damage location sensing system as in claim 17, further comprising means for operating said MFRR on a periodic basis to generate said harmonic response with periodic frequency wherein a plurality of harmonic responses are generated.

19. A wireless damage location sensing system as in claim 18, further comprising means for storing each of said harmonic responses so-generated.

20. A wireless damage location sensing system as in claim 19, further comprising means for time-stamping each of said harmonic responses so-stored.

21. A wireless damage location sensing system as in claim 17, further comprising a substrate to which said conductor is coupled.

22. A wireless damage location sensing system as in claim 17, wherein each of said arrangements of perforations comprises a closed geometric shape encompassing a continuous portion of said conductor.

23. A wireless damage location sensing system as in claim 17, wherein said conductor comprises a thin-film trace defining said geometric pattern, and wherein the width of said trace is selected from the group consisting of uniform and non-uniform and the spacing between adjacent portions of said trace is selected from the group consisting of uniform and non-uniform.

24. A wireless damage location sensing system as in claim 17, wherein said geometric pattern is a spiral.

* * * * *